United States Patent
Lizardi

(10) Patent No.: US 6,641,596 B1
(45) Date of Patent: Nov. 4, 2003

(54) KNOTLESS BIOABSORBABLE SUTURE ANCHOR SYSTEM AND METHOD

(75) Inventor: Jose' E. Lizardi, Franklin, MA (US)

(73) Assignee: Ethicon, Inc., Somerville, NJ (US)

( * ) Notice: Subject to any disclaimer, the term of this patent is extended or adjusted under 35 U.S.C. 154(b) by 302 days.

(21) Appl. No.: 09/691,685

(22) Filed: Oct. 18, 2000

(51) Int. Cl.[7] .............................................. A61B 17/04
(52) U.S. Cl. ......................................... 606/232; 606/72
(58) Field of Search ............................ 606/232, 72, 73, 606/88, 96, 86, 139, 144, 148, 224, 225, 222, 228; 411/75, 80, 354, 355, 511

(56) References Cited

U.S. PATENT DOCUMENTS

| | | |
|---|---|---|
| 65,499 A | 6/1867 | Miller |
| 1,082,540 A | 12/1913 | MacColl et al. |
| 3,708,883 A * | 1/1973 | Flander ........................ 433/174 |
| 4,007,743 A | 2/1977 | Blake |
| 4,378,019 A | 3/1983 | Yamada |
| 4,532,926 A | 8/1985 | O'Holla |
| 4,537,185 A | 8/1985 | Stednitz |
| 4,632,101 A | 12/1986 | Freedland |
| 4,721,103 A | 1/1988 | Freedland |
| 4,870,957 A | 10/1989 | Goble et al. |
| 4,898,156 A | 2/1990 | Gatturna et al. |
| 4,946,468 A | 8/1990 | Li |
| 4,976,715 A | 12/1990 | Bays et al. |
| 5,002,550 A | 3/1991 | Li |
| 5,013,316 A | 5/1991 | Goble et al. |
| 5,021,059 A | 6/1991 | Kensey et al. |
| 5,037,422 A | 8/1991 | Hayhurst et al. |
| 5,074,874 A | 12/1991 | Yoon, Inbae et al. |
| 5,084,050 A | 1/1992 | Draenert |
| 5,100,417 A | 3/1992 | Cerier et al. |
| 5,102,421 A | 4/1992 | Anspach, Jr. |
| 5,123,913 A | 6/1992 | Wilk et al. |
| 5,129,906 A | 7/1992 | Ross et al. |
| 5,129,912 A | 7/1992 | Noda et al. |
| 5,141,520 A | 8/1992 | Goble et al. |
| 5,152,765 A | 10/1992 | Ross et al. |
| 5,152,769 A | 10/1992 | Baber |
| 5,176,682 A | 1/1993 | Chow ........................ 606/72 |
| 5,178,629 A | 1/1993 | Kammerer |
| 5,192,303 A | 3/1993 | Gatturna et al. |
| 5,207,679 A | 5/1993 | Li |

(List continued on next page.)

FOREIGN PATENT DOCUMENTS

| | | | |
|---|---|---|---|
| FR | 2 784 020 | 10/1998 | ............. A61F/2/08 |
| WO | 9400079 | 1/1994 | |
| WO | WO 98/38938 | 9/1998 | ............. A61B/17/68 |
| WO | WO 99/42064 | 8/1999 | ............. A61F/41/00 |

Primary Examiner—A. Vanatta
(74) Attorney, Agent, or Firm—Nutter McClennen & Fish LLP

(57) ABSTRACT

A knotless suture system for anchoring tissue to bone is provided. The system includes a suture anchor configured to radially expand into bone. The suture anchor has a proximal end and a distal end with a bore formed therein. The system further includes a first loop of suture thread attached to the distal end of the suture anchor, a suture needle, and a second loop of suture thread attached to the needle and interlocked with the first loop of suture thread. The system also includes an expander pin that is configured and sized for insertion into the bore of the suture anchor, causing the anchor to radially expand from a first outer diameter to a second outer diameter. A method is also provided by which a detached tissue may be securely attached to bone in an anatomically correct position without the need to tie a knot.

65 Claims, 15 Drawing Sheets

U.S. PATENT DOCUMENTS

| | | | |
|---|---|---|---|
| 5,224,946 A | | 7/1993 | Hayhurst et al. |
| 5,226,535 A | | 7/1993 | Rosdhy et al. |
| 5,236,431 A | | 8/1993 | Gogolewski et al. |
| 5,236,445 A | | 8/1993 | Hayhurst et al. |
| 5,258,016 A | | 11/1993 | DiPoto et al. |
| 5,259,846 A | | 11/1993 | Granger et al. |
| 5,261,914 A | | 11/1993 | Warren |
| 5,268,001 A | * | 12/1993 | Nicholson et al. ............ 606/72 |
| 5,281,236 A | | 1/1994 | Bagnato et al. |
| 5,282,809 A | | 2/1994 | Kammerer et al. |
| 5,306,290 A | | 4/1994 | Martins et al. |
| 5,320,629 A | | 6/1994 | Noda et al. |
| 5,356,413 A | | 10/1994 | Martins et al. |
| 5,358,511 A | | 10/1994 | Gatturna et al. |
| 5,370,661 A | | 12/1994 | Branch |
| 5,370,662 A | | 12/1994 | Stone et al. |
| 5,372,146 A | | 12/1994 | Branch |
| 5,372,599 A | | 12/1994 | Martins |
| 5,380,334 A | | 1/1995 | Torrie et al. |
| 5,383,905 A | | 1/1995 | Golds et al. |
| 5,400,805 A | | 3/1995 | Warren |
| 5,405,354 A | | 4/1995 | Sarrett |
| 5,417,712 A | | 5/1995 | Whittaker et al. |
| 5,464,427 A | | 11/1995 | Curtis et al. ................. 606/232 |
| 5,500,000 A | | 3/1996 | Feagin et al. |
| 5,534,011 A | | 7/1996 | Greene, Jr. et al. |
| 5,545,180 A | | 8/1996 | Le et al. |
| 5,569,306 A | | 10/1996 | Thal |
| 5,578,057 A | | 11/1996 | Wenstrom, Jr. |
| 5,584,860 A | | 12/1996 | Goble et al. |
| 5,618,314 A | | 4/1997 | Harwin et al. |
| 5,707,395 A | * | 1/1998 | Li .............................. 606/232 |
| 5,709,708 A | * | 1/1998 | Thal ........................... 606/232 |
| 5,782,864 A | | 7/1998 | Lizardi |
| 5,814,051 A | | 9/1998 | Wenstrom, Jr. |
| 5,814,071 A | * | 9/1998 | McDevitt et al. ............ 606/232 |
| 5,860,978 A | * | 1/1999 | McDevitt et al. ............. 606/72 |
| 5,871,504 A | * | 2/1999 | Eaton et al. ................. 606/232 |
| 5,891,168 A | * | 4/1999 | Thal ........................... 606/232 |
| 5,899,921 A | * | 5/1999 | Caspari et al. ............... 606/232 |
| 5,935,129 A | * | 8/1999 | McDevitt et al. ............. 606/72 |
| 6,056,772 A | * | 5/2000 | Bonutti ....................... 606/232 |
| 6,200,329 B1 | * | 3/2001 | Fung et al. .................. 606/232 |
| 6,319,252 B1 | * | 11/2001 | McDevitt et al. ............. 606/60 |

\* cited by examiner

KNOTLESS BIOABSORBABLE SUTURE ANCHOR SYSTEM AND METHOD

CROSS-REFERENCE TO RELATED APPLICATIONS

Not applicable.

STATEMENT REGARDING FEDERALLY SPONSORED RESEARCH

Not Applicable.

1. Field of the Invention

The invention relates generally to medical devices and procedures. More particularly, this invention relates to a knotless bioabsorbable suture anchor system for attaching soft tissue to bone, and to methods for attaching soft tissue to bone.

2. Background of the Invention

Soft tissues, such as ligaments, tendons and muscles, are attached to a large portion of the human skeleton. In particular, many ligaments and tendons are attached to the bones which form joints, such as shoulder and knee joints. A variety of injuries and conditions require attachment or reattachment of a soft tissue to bone. For example, when otherwise healthy tissue has been torn away from a bone, surgery is often required to reattach the tissue to the bone to allow healing and a natural reattachment to occur.

A number of devices and methods have been developed to attach soft tissue to bone. These include screws, staples, cement, suture anchors, and sutures alone. Some of the more successful methods involve the use of a suture anchor to attach a suture to the bone, and tying the suture in a manner that holds the tissue in close proximity to the bone.

The tissue may be attached to the bone during open surgery, or during closed (e.g., arthroscopic) surgical procedures. Closed surgical procedures are preferred since they are less invasive and are less likely to cause patient trauma. In a closed surgical procedure, the surgeon performs diagnostic and therapeutic procedures at the surgical site through small incisions, called portals, using instruments specially designed for this purpose. One problem encountered in the less invasive, closed surgical procedures is that the surgeon has significantly less room to perform the required manipulations at the surgical site. Thus, devices and methods are needed which will allow a surgeon to effectively and easily attach tissue to bone in the small spaces provided by less invasive surgical procedures.

Conventional methods for attaching soft tissue to bone typically require that the surgeon tie a knot in the suture thread to attach the suture to an anchor, or to attach the tissue to the bone using the suture. Knot tying at the surgical site in closed surgical procedures, and even in open surgery, is difficult and time consuming due to inherent space constraints. Further, knots and other bulky attachment means can irritate tissue over time.

Knotless suture anchor systems have been developed for use with closed surgical procedures, and U.S. Pat. No. 5,569,306 provides one example of such a system. Although generally useful, such systems can be limited to use only with certain types or shapes of tissue, or to use with certain anatomical structures. Proper attachment of soft tissue requires that it be placed in the anatomically correct position to promote optimal healing.

A further knotless suture anchor system is disclosed in U.S. Pat. No. 5,782,864. While useful, the suture anchor and system disclosed in this patent is not believed to be absorbable. That is, the suture anchor is made of a metal, which will remain permanently implanted in the patient.

Further, some conventional knotless suture anchor systems may require, in order to attach a broader array of tissue shapes to bone, that the suture anchor pass though the tissue to be attached. This is undesirable because it unnecessarily irritates the injured tissue and it requires opening a much larger hole in the tissue.

There is thus a need for an improved system for anchoring soft tissue to bone which reduces or eliminates the need to tie suture knots at the surgical site. Further, there is a need for an improved system for anchoring soft tissue to bone which is fast and easy to deploy. It would also be advantageous to provide at least a partially absorbable knotless suture anchor and system so as to encourage natural regrowth of the damaged or torn tissue.

SUMMARY OF THE INVENTION

The present invention provides a knotless suture system for anchoring tissue to bone. The system includes a suture anchor configured to radially expand into bone. The suture anchor has a proximal end and a distal end with a bore formed therein. The system further includes a first loop of suture thread attached to the distal end of the suture anchor, a suture needle, and a second loop of suture thread attached to the needle and interlocked with the first loop of suture thread. The system also includes an expander pin that is configured and sized for insertion into the bore of the suture anchor, causing the anchor to radially expand from a first outer diameter to a second outer diameter. A method is also provided by which a detached tissue may be securely attached to bone in an anatomically correct position without the need to tie a knot.

In one embodiment, the system includes a suture anchor having proximal and distal ends, wherein a suture-engaging tip is present at the distal end and a separate, radially expandable sleeve, having a bore formed longitudinally therethrough, forms a proximal end of the suture anchor. The tip and the sleeve are mated to one another, such as by a threaded engagement. The system further includes an expander pin for insertion into the bore of the expandable sleeve. In this embodiment, the expandable sleeve may include two substantially flat, opposed sides between the proximal and distal ends and separated by the bore. As noted above, the system includes a first loop of suture thread attached to the tip, a second loop of suture thread interlocked with the first loop, and a suture needle having a first, tissue penetrating end and a second, trailing end attached to the second loop. In one embodiment, the expander pin is made from a bioabsorbable material.

In another embodiment, the system comprises a suture anchor which includes a unitary base member having a distal end and a proximal end with a bore formed longitudinally therein, and a separate expander pin for insertion into the bore of the base member to effect radial expansion of at least a portion of the base member. The distal end of the base member has a suture thread-engaging groove for seating a portion of the first loop of suture thread. Additionally, the base member can have two substantially flat, opposed sides between the distal and proximal ends to allow suture thread to easily pass around the base member. The flat sides can each contain a longitudinally oriented slit, which may be matable with the protrusions on opposite sides of the expander pin. Preferably, the base member and expander pin are formed from a bioabsorbable material.

In an embodiment that is particularly useful in closed surgery, the second suture loop is formed using a suture loop closure and is attached to a hollow suture needle by means of a slot provided in a wall of the hollow needle. This embodiment may also employ an actuator, disposed within the hollow needle, which can be selectively deployed to disengage the second suture loop from the needle. The hollow needle used with this embodiment preferably is part of an elongate tool, such as a suture inserter, that is useful in closed surgical procedures. The hollow needle typically forms the distal end of such a tool.

Various types of inserter tools are also included with the system of the invention. The inserter tool generally includes an elongate shaft element, and a pusher or actuation element may be slidably mounted on the shaft Actuation of the pusher causes the expander pin to be disposed within the bore of the radially expandable sleeve or proximal component of the anchor to effect radial expansion.

The system may be used in a method wherein the suture needle and the attached second suture loop are passed through a detached segment of tissue. The second suture loop is pulled through the detached tissue until a portion of the interlocked first suture loop extends through the detached tissue. The suture anchor is then maneuvered so that a portion of the first suture loop is seated within a suture-engaging groove at the distal end of the suture anchor. The anchor is then inserted into a predrilled bore in a portion of bone. Once the suture anchor is inside the bone, the expander pin is driven into the bore of the suture anchor, expanding the base radially to the extent that external walls of the suture anchor engage bone. The suture anchor is stabilized in a friction fit within the bore, and the detached tissue is thereby attached to the bone in the desired position.

The term "suture needle" is used herein to encompass both conventional suture needles, used in open surgical procedures, as well as suture needles that may form a hollow, distal end of an elongate tool useful with closed surgical procedures.

Further features of the invention, its nature and various advantages, will be more apparent from the accompanying drawings and the following detailed description of the drawings and the preferred embodiments.

DETAILED DESCRIPTION OF THE INVENTION

Figure 1:
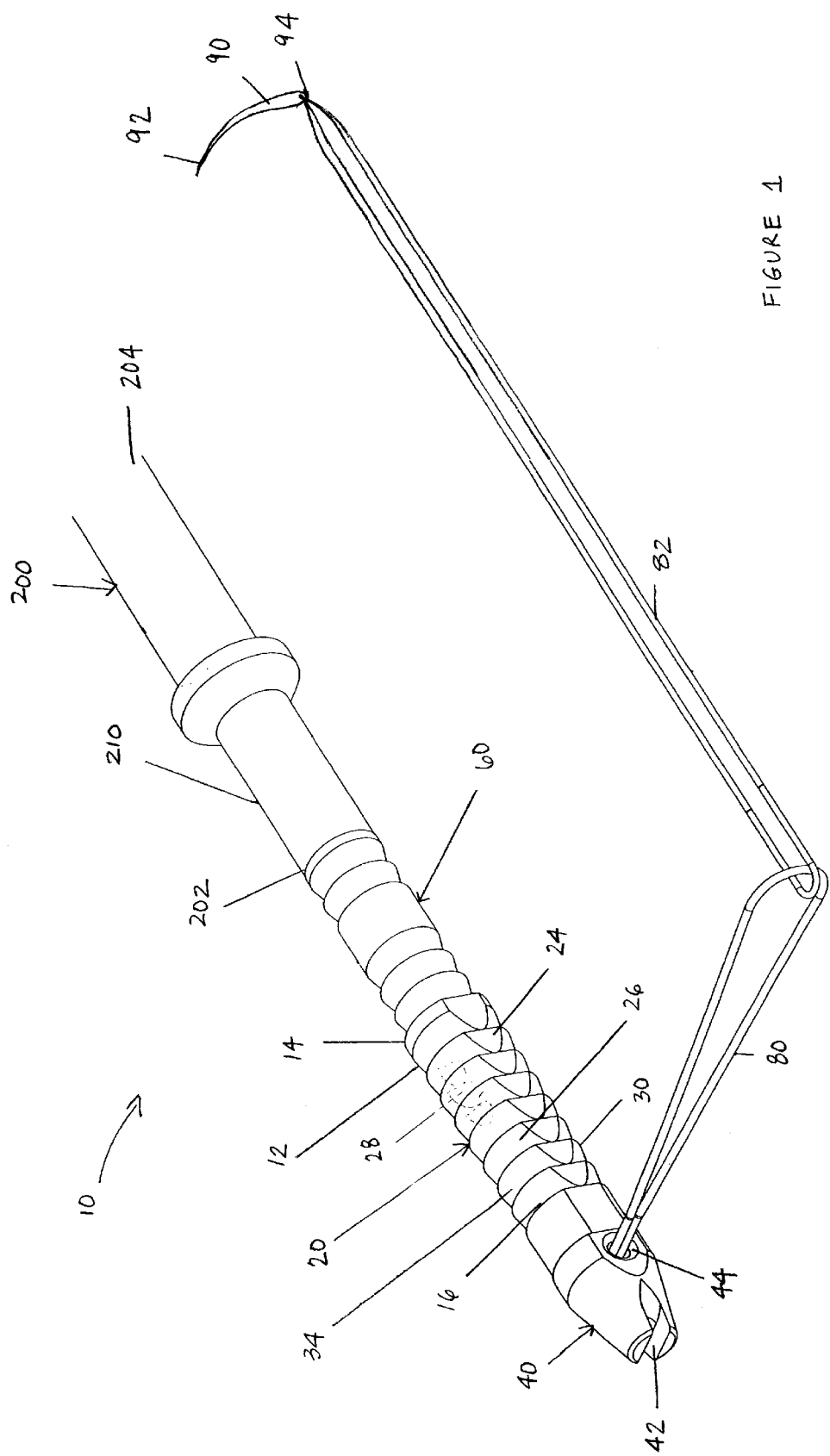
FIG. 1 is a perspective view of an exemplary suture anchor system of the invention attached to a portion of an inserter tool.
Figure 2:
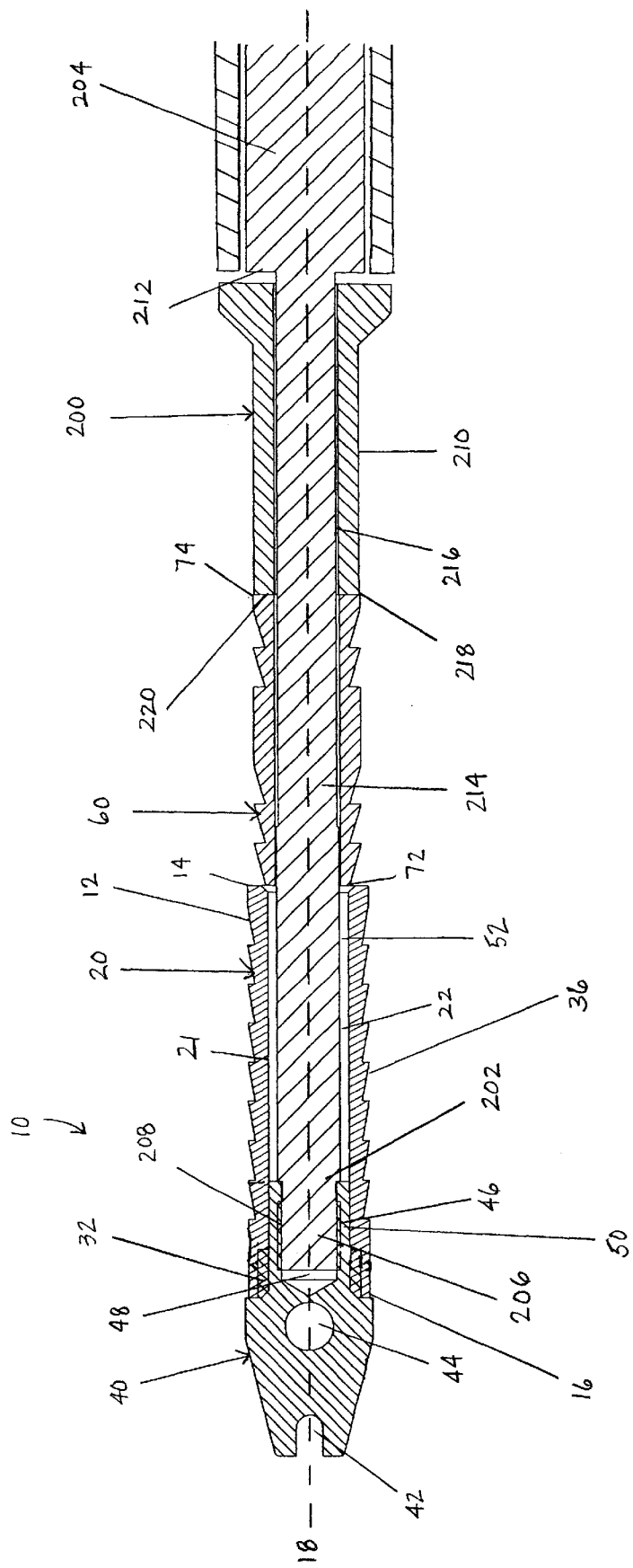
FIG. 2 is a cross-sectional view of the suture anchor system of FIG. 1.
Figure 2A:
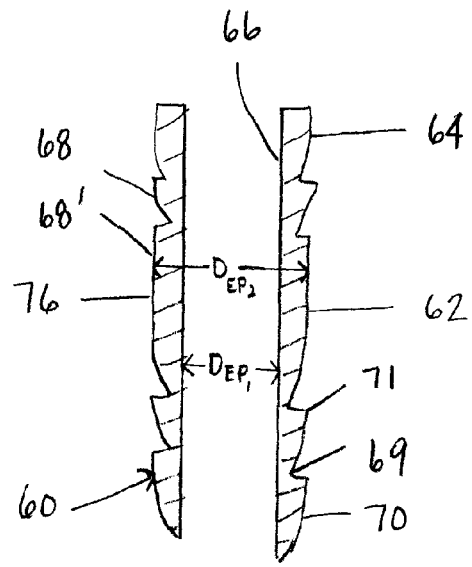
FIG. 2A is an exploded view of the suture anchor system of FIG. 2.
Figure 2A:
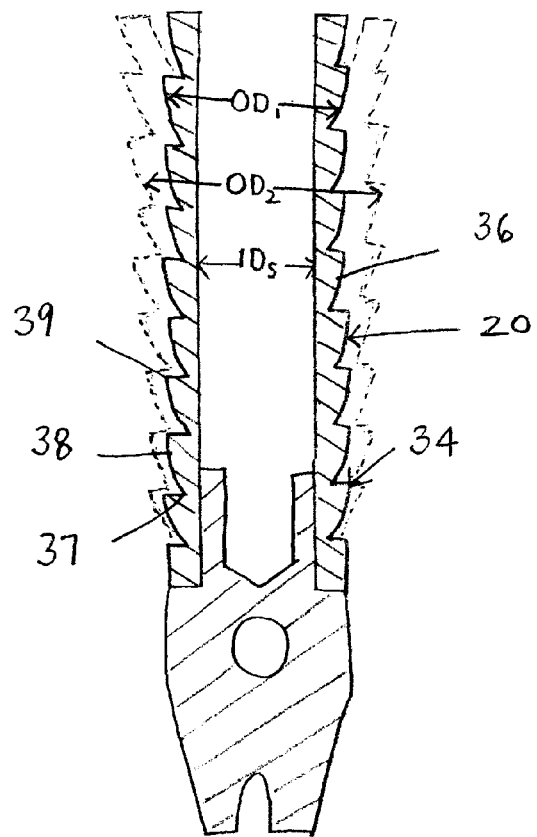

Referring now to FIGS. 1 through 2A, a system for anchoring tissue to bone in accordance with the invention is shown. The system 10 includes a suture anchor 12 configured to radially expand into bone. The suture anchor 12 has a proximal end 14 and a distal end 16 having a bore 22 that extends along a longitudinal axis 18 thereof. The suture anchor 10 includes a suture-engaging tip 40 at the proximal end 14 and a separate, radially expandable sleeve 20 at the distal end 16. The system of FIG. 1 also includes a first suture loop 80 attached to the suture-engaging tip 40, a suture needle 90, and a second suture loop 82 attached to the suture needle 90. The first suture loop 80 and second suture loop 82 are interlocked with each other. The system also includes an expander pin 60 that is configured and sized for insertion into the bore 22 of the expandable sleeve 20, causing the suture anchor 10 to radially expand from a first diameter to a second diameter.

The sleeve 20 is attached to the suture-engaging tip 40 and forms the proximal end 14 of the suture anchor 10. The expandable sleeve 20 can include two substantially flat, longitudinally extending portions 24, 28 formed on opposite sides of the sleeve 20, between the proximal end 14 and distal end 16 of the sleeve 20, to allow for suture thread to easily pass back and forth. Although sides 24, 28 are shown as flat, it is understood that they may be otherwise shaped or contoured. For example, they may be curved or rounded. The sides 26, 30 that are adjacent to sides 24, 28 may be curved, rounded, or flat.

Suture engaging tip 40 includes at a distal end a suture-thread engaging groove 42, and intermediate the distal and proximal ends of the tip 40 is a through hole 44 for attaching suture thread. Suture-engaging groove 42 is configured for seating a portion of the first loop 80. The tip 40 is preferably mated to the sleeve 20. Preferably, as shown in FIG. 2, tip 40 is threadingly engaged to the distal end 16 of expandable sleeve 20. As illustrated, a proximal end of tip 40 includes an external threaded region 46 and a distal end of the sleeve 20 includes a complementary internal threaded region 32 which is sized and shaped to matingly receive the threaded portion 46 of tip 40. Although FIG. 2 illustrates external threads 46 on tip 40 mating with internal threads 32 of the sleeve 20, one of ordinary skill in the art will appreciate that other configurations may be used as required.

As further shown in FIGS. 1 and 2, the system includes an expander pin 60 configured and sized to be inserted into the bore 22 of the sleeve 20 in an interference fit. Expander pin 60 has an outer diameter which is slightly larger than the inner diameter of bore 22. When expander pin 60 is fully seated within bore 22, the expandable sleeve 20 radially expands so as to engage the walls of the bore. The radial expansion of the sleeve 20 causes the sleeve to transition from a first diameter to a second, larger diameter. The difference between the first and second diameters is generally in the range of about 1.0 mm to 1.5 mm.

The expandable sleeve 20 preferably includes one or more external surface features 34 that enhance the bone engaging properties of the sleeve 20. As shown in detail in FIG. 2A, the external surface features 34 may be in the form of several, adjacent ramped ridges 36. Each ridge has a distal portion 37 and a raised, proximal portion 39. The surface connecting the distal and proximal portions 37, 39 of each ridge 36 preferably is a continuous surface 38 that is disposed at an angle with respect to longitudinal axis 18 in the range of about 9 to 11 degrees. In one embodiment, the difference in height between the distal and proximal portions 37, 39 of each ridge 36 is in the range of about 1.4 to 0.75 mm. The distal facing surface 38 of each ridge 36 is in the form of an endwall that is preferably oriented to be substantially perpendicular to the longitudinal axis 18 of the suture anchor 10. It is understood, however, that the endwall may be slightly overcut or undercut.

In the illustrated embodiment, the sleeve 20 has approximately eight ridges 36. It is understood that as few as one or two ridges may be present, and that more than eight ridges may be present.

The expansion pin 60 also has one or more positive surface features 62 formed on an external surface 64 thereof. The surface features are preferably wedge-like fins 68, or tapered ridges, that are non-deformable.

Each wedge-like fin 68 of the expansion pin 60 has a ramped surface which increases in height from a distal end 69 to a proximal end 71 thereof. The surface 70 connecting the distal and proximal ends 69, 71 is continuous and is preferably oriented at an angle (with respect to longitudinal axis 18) in the range of about 15 to 17 degrees. The differential in height between the distal end 69 and the proximal end 71 of each fin 68 is in the range of about 1.5 to 1.6 mm.

As illustrated in FIGS. 1 through 2A, the fins 68 are disposed on the expansion pin 60 adjacent to one another. The expansion pin 60 may include a single fin or it may have several. As shown in FIG. 2, one or more fins may have an extended distal end. For example, fin 68' includes an extended distal surface 76 that runs parallel with longitudinal axis 18 over a distance of about 0.4 to 0.6 mm.

The distal facing surface 76 of each fin 68, 68' is in the form of an endwall that is preferably oriented to be substantially perpendicular to the longitudinal axis 18 of the suture anchor. It is understood, however, that the endwall may be slightly overcut or undercut.

The suture anchor 12 may be constructed from suitable materials known to those of ordinary skill in the art. In one embodiment, expandable sleeve 20 is constructed from a polymeric material that is substantially rigid, yet able to withstand a force that expands the diameter of the sleeve 20 by about 30% without failing. Examples of suitable materials include high density polyethylene and polypropylene. Tip 40 is constructed from a suitable metal such as medical grade stainless steel or titanium alloy. Alternatively, tip 40 can be constructed from a polymer such as polylactic acid or polysulfone. Expander pin 60 is preferably formed from a bioabsorbable material, such as polylactic acid (PLA) and polysulfone.

The system may also include an anchor insertion tool of the type commonly used in the art. A portion of an insertion tool 200 suitable for deployment of the suture anchor 10 of this invention is illustrated in relevant part in FIGS. 1 and 2. Insertion tool 200 includes a distal end 202 having a tip 206 with an external threaded portion 208 which is sized and shaped to matingly engage with the internal threaded portion 50 of tip 40. As shown in FIG. 2, tip 40 includes a bore 48 having an internal threaded portion 50 therein which is adapted to mate with the external threaded portion 208 of the tool 200. In some embodiments, the suture anchor 10 may be removably premated to the distal end 202 of the insertion tool 200.

The insertion tool 200 also includes an elongate shaft 214 that is proximal of the distal end 202. The shaft 214 is adapted to receive the expandable sleeve 20 and the expander pin 60 in a clearance fit. As shown in FIG. 2, an annular gap 52 is present between the outer surface 215 of the shaft 214 and an inner surface 21 of the sleeve 20. The expander pin 60, which is mounted on the shaft 214 proximally adjacent to and abutting sleeve 20, is also mounted on the shaft 214 in a clearance fit that enables the expander pin 60 to slide distally on the shaft 214 to occupy and expand the gap 52. A pusher member 210 may be mounted on the shaft 214 proximally adjacent to a distal end 72 of expander pin 60. The distal end 218 of the pusher member 210 includes a face 220 that abuts the expander pin 60, transferring a force thereto that permits the expander pin 60 to slide within gap 52. One of ordinary skill in the art will appreciate the force necessary to move the pusher member 210 and the expander pin 60 distally may be provided by a variety of mechanisms that are known in the art.

The gap 52 preferably has dimensions in the range of 0.2 to 0.4 mm before being expanded by the action of expander pin 60. As illustrated in FIG. 2A, the diameter of the expander pin 60 at a distal (smallest) end ($D_{EP1}$) of wedge-like fins 68 is preferably about equal to inner diameter ($ID_S$) of sleeve 20. The diameter of the expander pin 60 at its widest dimension ($D_{EP2}$), measured at the distal ends 69 of wedge-like fins 68, is in the range of about 4.0 to 4.2 mm. Thus, as the expander pin 60 is forced into gap 52, the sleeve 20 radially expands from a first outside diameter ($OD_1$) to a second outside diameter ($OD_2$).

One of ordinary skill in the art will readily appreciate that the dimensions of the various components of the system 10 may vary depending upon the desired surgical applications. Generally, however, the expandable sleeve 20 has a length of about 10 to 20 mm and a first outer diameter ($OD_1$) of about 4.5 to 4.7 mm. The outer diameter ($OD_1$) of the sleeve 20 will increase during use to a second outer diameter ($OD_2$), discussed above, to about 5.5 to 6.0 mm. The expander pin 60 preferably has a length in the range of about 5 to 15 mm. The tip 40 preferably has a length in the range of about 5.0 to 6.0 mm.

As noted above, the tool 200 includes a distal end 202 with external threads 208 that mate with the internal threads 50 of the tip 40. This arrangement firmly secures the suture anchor 10 to the tool 200. Thus, when the pusher member 210 is actuated, moving expansion pin 60 distally, the suture anchor 12 is not able to move distally. As force is continued to be applied by the pusher member 210, the expansion pin 60 moves into the gap 52 between the shaft 214 and the internal surface 21 of the sleeve 20. This causes radial expansion of the sleeve 20. When the expander pin 60 is securely positioned inside the bore 22 of the sleeve 20, the tool can be removed by unscrewing the threaded portion 208 of the tip 206 of tool 200 from the internal threads 50 of the tip 40.

Figure 3:
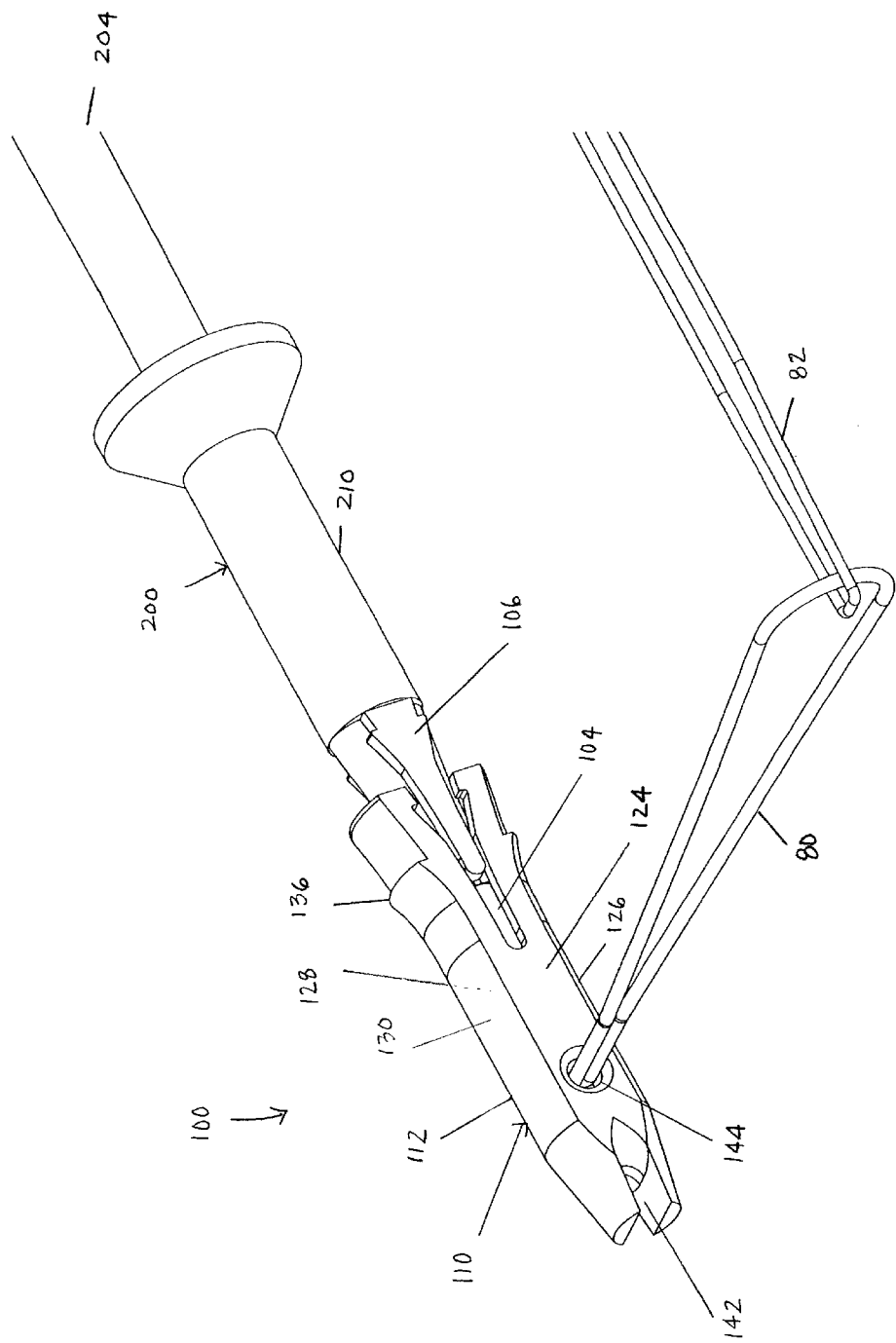
FIG. 3 is a perspective view of another exemplary suture anchor system of the invention attached to a portion of an inserter tool.
Figure 4:
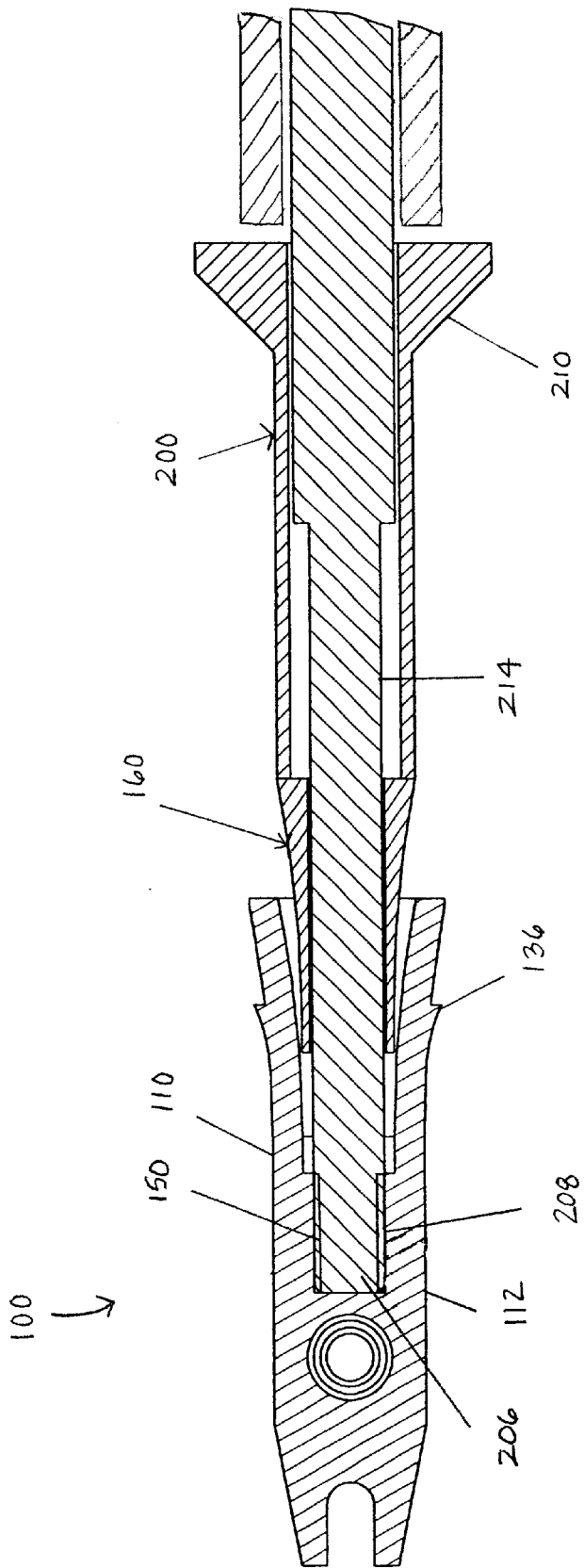
FIG. 4 is a cross-sectional view of the suture anchor system of FIG. 3.

In another embodiment, the suture anchor can be formed from a single piece of material. For example, FIGS. 3 and 4 show another exemplary embodiment wherein the system 100 includes a suture anchor 110 comprises a unitary expandable base member 112. Expandable base member 112 is similar to expandable sleeve 20 of suture anchor 10, and includes similar elements, which are designated with the prefix "1" (e.g., through hole 44 of suture anchor 12 is designated through hole 144 for suture anchor 110). Key features and distinctions are highlighted hereinbelow.

Figure 4A:
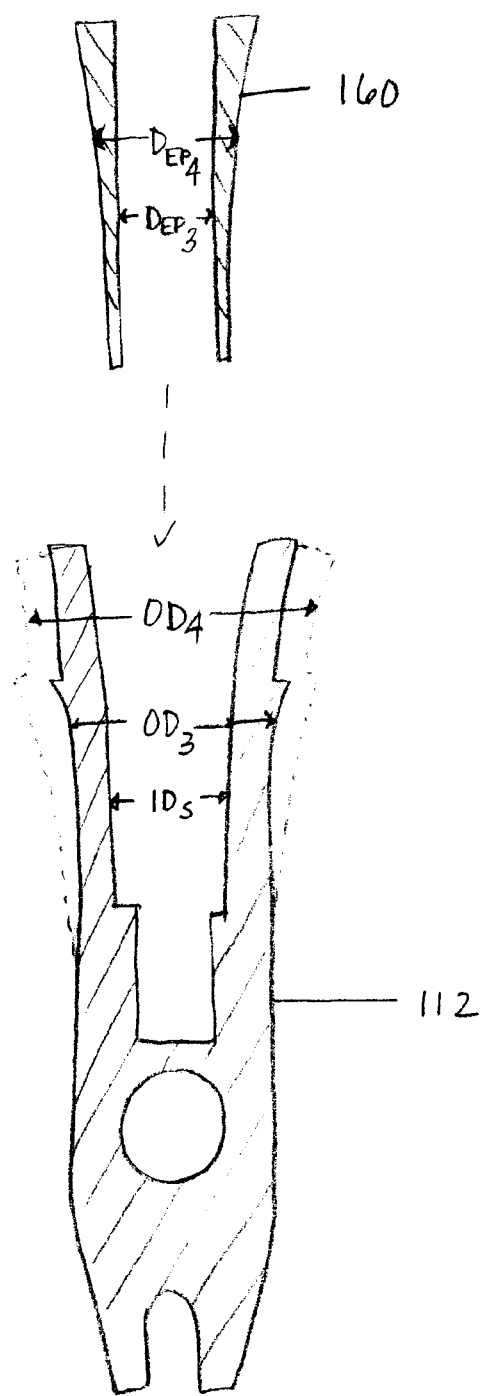
FIG. 4A is an exploded view of the suture anchor system of FIG. 4.

As shown in FIGS. 3 through 4A, suture anchor 110 includes an expandable base member 112 having a proximal end 114 and a distal end 116. The proximal end 114 has a bore 122 extending longitudinally therethrough. The distal end 116 of base member 112 includes a suture thread-engaging groove 142. The system 100 used with suture anchor 110 and illustrated in FIG. 3 also includes a first suture loop 80 attached to the distal end 116 of the expandable base member 112 by a through hole 144, a suture needle 90, and a second suture loop 82 attached to the suture needle and interlocked with the first suture loop 80. Suture thread-engaging groove 142 is configured for seating a portion of the first loop 80. The system 100 also includes an expander pin 160 that is configured and sized for insertion into the bore 122 of the expandable base member 110, causing the suture anchor 100 to radially expand from a first diameter to a second diameter.

The expandable base member 112 can include two substantially flat, longitudinally extending portions 124, 128 formed on opposite sides of the base member 112 to allow for suture thread to easily pass back and forth. Although sides 124, 128 are shown as flat, it is understood that they may be otherwise shaped or contoured. For example, they may be curved or rounded. The sides 128, 130 that are adjacent to sides 124, 128 may be curved, rounded, or flat.

In addition, sides 124, 128 may include slits 104 that will allow for easy expansion of the anchor base 110. As shown in FIG. 4, the expansion pin 160 of this system includes complementary protrusions 106 on opposed sides which are sized and shaped to matingly engage and seat within the slits 104 of the base member 112 when fully inserted into the bore 122. Preferably, the protrusions 106 irreversibly interlock with slits 104.

As further shown in FIGS. 3 and 4, the system includes an expander pin 160 configured and sized to be inserted into the bore 122 of the expandable base member 112 in an interference fit. Expander pin 160 has an outer diameter which is slightly larger than the inner diameter of bore 122. In one embodiment shown in FIGS. 4 and 4A, the outer surface of expander pin 160 tapers from the proximal end 174 to the distal end 172 such that, from a cross-sectional view, the expander pin 160 has a flared, proximal end.

When expander pin 160 is fully seated within bore 122, the expandable base member 112 radially expands so as to engage the walls of the bore. The radial expansion of the base member 112 causes the anchor 100 to transition from a first diameter to a second, larger diameter. The difference between the first and second diameters is generally in the range of about 1.0 mm to 2.0 mm.

The expandable base member 112 preferably includes one or more external surface features 134 that enhance the bone engaging properties of the base member 112. The external surface features 134 may be in the form of several, adjacent ramped ridges 136, similar to the ridges 36 of anchor 10 that are described above.

The expansion pin 160 also has one or more positive surface features formed on an external surface thereof (not shown). The surface features are preferably wedge-like fins, or tapered ridges, that are non-deformable. The wedge-like fins are similar to fins 68 of anchor 10 that are described above.

The suture anchor 110 and system 100 may be constructed from suitable materials known to those of ordinary skill in the art. In one embodiment, expandable base member 112 is constructed from a polymeric material that is substantially rigid, yet able to withstand a force that expands the diameter of the base member 112 by about 30% without failing. Preferably, expandable base member 112 and expander pin 160 are formed from a bioabsorbable material, such as polylactic acid (PLA) and polysulfone.

FIG. 4 shows a cross-sectional view of the suture anchor 110 and system 100 attached to a portion of the exemplary insertion tool 200 described above. As shown, expandable base member 112 includes a bore 122 having internal threads 150 formed therein, which are adapted to mate with the external threaded portion 208 of the tool 200. In some embodiments, the suture anchor 100 may be removably premated to the distal end 202 of the insertion tool 200. Although FIG. 4 illustrates external threads 208 on tip 206 mating with internal threads 150 of the base member 112, one of ordinary skill in the art will appreciate that other configurations may be used as required. In some embodiments, the suture anchor 100 may be removably premated to the distal end 202 of the insertion tool 200.

As shown in FIG. 4, the shaft 214 of insertion tool 200 is adapted to receive the expandable base member 112 and the expander pin 160 in a clearance fit. An annular gap 152 is present between the outer surface 215 of the shaft 214 and an inner surface 121 of the base member 112. The expander pin 60, which is mounted on the shaft 214 proximally adjacent to and abutting base member 112, is also mounted on the shaft in a clearance fit such that the expander pin 160 is able to slide distally on the shaft 214 to occupy and expand the gap 152. A pusher member 210 may be mounted on the shaft 214 proximally adjacent to a distal end 172 of expander pin 160. The distal end 218 of the pusher member 210 includes a face 220 that abuts the expander pin 160, transferring a force thereto that permits the expander pin 160 to slide within gap 152. One of ordinary skill in the art will appreciate the force necessary to move the pusher member 210 and the expander pin 160 distally may be provided by a number of mechanisms that are known in the art.

In use, the first suture loop 80 may be suitably attached to the suture anchor 12, 110 through one or more through holes 44, 144 that are formed in the body of the suture anchor 12, 110, and which extend transversely to longitudinal axis 18. In the exemplary suture anchors 12, 110, the first suture loop 80 is attached substantially at distal ends 16, 116 of the anchor 12, 110, and portions of first suture loop 80 extend past the proximal ends 14, 114 on opposed sides of the suture anchor 12, 110.

Through hole 44, 144 is adapted, by providing varying diameters within the through hole 44, 144, to retain the first suture loop 80. For example, the diameter within the hole 44 can be varied by providing an annular collar (not shown) therein. The inner diameter of the annular collar can be large enough to allow the unknotted portion of the first suture loop 80 to pass through the inner diameter. However, the inner diameter is small enough to prevent the knot from passing through the through hole 44, 144. When the unknotted portion of the first suture loop 80 is drawn through the hole 44, 144 the knot is retained by the annular collar and the first suture loop 80 is thereby attached to the tip 40.

The first suture loop 80 may be attached to the suture anchor by tying two free ends of a suture thread into a knot (not shown). It will be understood that one may use other methods of attaching the two free ends, including the use of suture loop closure devices as further described below with regard to the second suture loop.

The first suture loop 80 may be constructed from thread suitable for use as a suture. A variety of suture materials are well known to those of ordinary skill in the art. Exemplary materials include braided polyester and polydioxanone (PDS).

The length of the first suture loop 80 may be determined by a person of ordinary skill in the art, depending upon the desired applications of the system. This dimension depends, to a large extent, upon the dimensions of the tissue to be attached, the type of surgery to be performed, and whether an open or closed surgical technique is to be used. By way of example, the length of the first suture loop may range from about one quarter to one and one half inch in procedures to repair a Bankart lesion or a rotator cuff tear. In an exemplary embodiment, as used in the method described herein below, the length of the first suture loop 80 is about one half inch.

Referring again to FIG. 1, the suture needle 90 has a first, tissue penetrating end 92 and a second trailing end 94. The size and shape of the needle used with the system of the invention may be selected by a person of ordinary skill in the art depending upon the specific application of the system, and in particular, depending upon whether the system is used in an open or closed (e.g., arthroscopic) surgical procedure. Generally, needle 90 is at least slightly curved.

In the exemplary embodiment of FIG. 1, which is typically used in open surgical procedures, the second suture loop 82 is attached to the suture needle 90 at the second end 94 of needle 90. One of ordinary skill in the art will appreciate that a number of techniques can be utilized to join the second suture loop 82 to the suture needle 90. For example, the second end 94 of the suture needle 16 can be hollowed so that two free ends of suture thread may be inserted therein. The hollowed end is then crimped to securely retain the two ends of suture thread within the second end 94 of the needle 90, thus creating the second suture loop 18.

Figure 5:
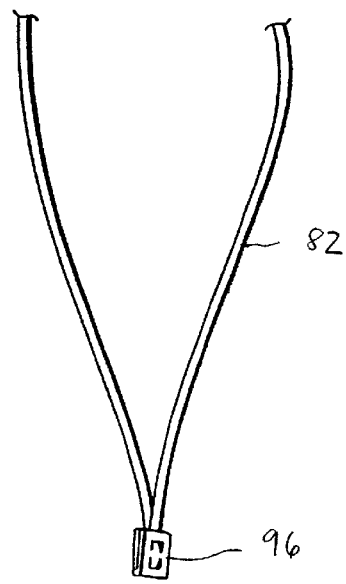
FIG. 5 is a partial view of a second suture loop with a suture loop closure.
Figure 6:
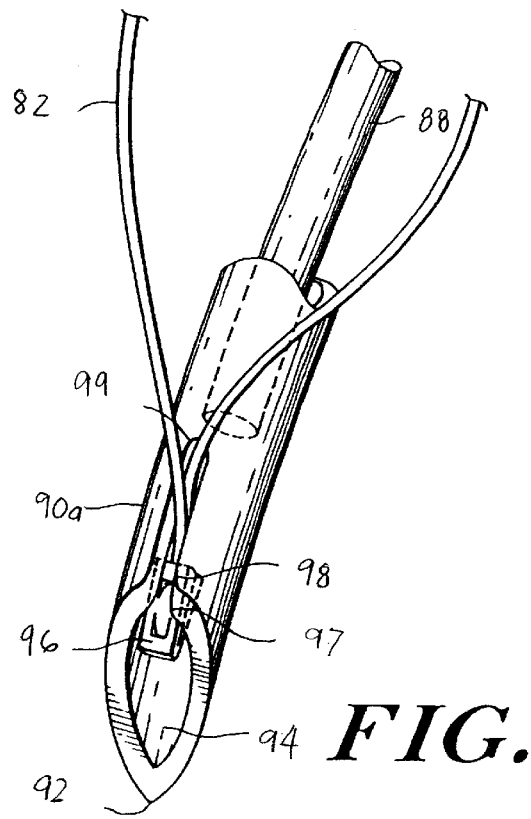
FIG. 6 is a partial view of the second suture loop and suture loop closure of FIG. 5 engaged with a suture needle.

In an alternative embodiment, shown in FIGS. 5 and 6, that is particularly suited for use in closed surgical procedures the second suture loop 82 may be attached to the needle 90*a* by means of a suture loop closure 96. Referring now to FIG. 5, the second suture loop 82 may be formed by attaching two free ends of a length of suture thread within a suture loop closure 96. The suture loop closure 96 may consist of a metal tube having an internal diameter large enough to admit two ends of suture thread. The two free ends of the suture thread are then entered into the suture loop closure 96 and the suture loop closure 96 is crimped to retain the ends of the suture thread and form the second suture loop 82. It will be understood that the suture loop closure 96 may take other forms, including a knot tied with the two free ends of the suture thread.

A second suture loop 82, having a suture loop closure 96, may be attached to a suture needle 90*a* as shown in FIG. 6. In this exemplary embodiment, the suture needle 90*a* is a hollow member, having an open distal end 94, one wall of which includes a tissue-penetrating edge or point 92. A slot 98 is formed in the wall of the distal end of the needle, preferably opposite point 92. The slot 98 has an open end 97 that communicates with the open distal end 94 of the suture needle 90 and an opposite, closed end 99. The slot 98 is wide enough to slidably engage the second suture loop 82, but narrow enough to retain the suture loop closure 96 on one side of the slot 98. The second suture loop 82 is then attached to the suture needle 90*a* by placing the suture loop closure 96 inside the open first end 97 of the hollow suture needle 90*a* and sliding the suture loop closure 96 and the attached second suture loop 82 within the slot 98 to the closed end 99 thereof.

The hollow suture needle 90*a* of FIG. 6 may also include an internally disposed actuator 88. The actuator 88 may be a rod that is selectively slidable within the hollow suture needle 90*a* between a first position, in which the actuator 88 is inside the hollow needle 90*a* and does not reach the slot 98, and a second position (not shown), in which the actuator 88 extends past the slot 98. Selectively sliding the actuator 88 from the first position to the second position causes the actuator 88 to contact the suture loop closure 96 (and the attached second suture loop 82), causing closure 96 to slide the length of slot 98 and become disengaged from the needle 90.

Suture needle 90*a*, as noted above, is well suited for use in closed surgical procedures. The suture needle 90*a* may form the distal end of an elongate suture inserter tool (e.g., an arthroscopic, laparoscopic or endoscopic tool) that is useful in closed surgical procedures.

The second suture loop 82, like the first suture loop 80, may be constructed from well known materials suitable for use as a suture. The length of the second suture loop may be determined by a person of ordinary skill in the art depending upon factors such as the dimensions of the tissue to be attached, the type of surgery to be performed, and whether an open or closed surgical technique is to be used. For example, the length of second loop 82 is generally in the range of about 20 to 40 inches, and more preferably about 30 to 36 inches for closed surgical procedures. Open surgical procedures can utilize a smaller length for second loop 18, in the range of about 6 to 12 inches and more preferably 8 to 10 inches.

The systems 10, 100 of the invention for anchoring tissue to bone may be used in the method described herein below. For purposes of illustration, FIGS. 7–14 depict the method of using suture anchor 12 in the context of arthrosporic shoulder repair, more specifically, attaching a detached labrum (as might result from a Bankart lesion or rotator cuff tear) to the glenoid rim of a scapula. It will be understood, however, that the system and method described herein are equally applicable to connecting detached tissue in other contexts as well. Further, the method described is merely exemplary of the steps involved in both systems and is equally suitable for the system 100 of suture anchor 110 as well.

Figure 7:
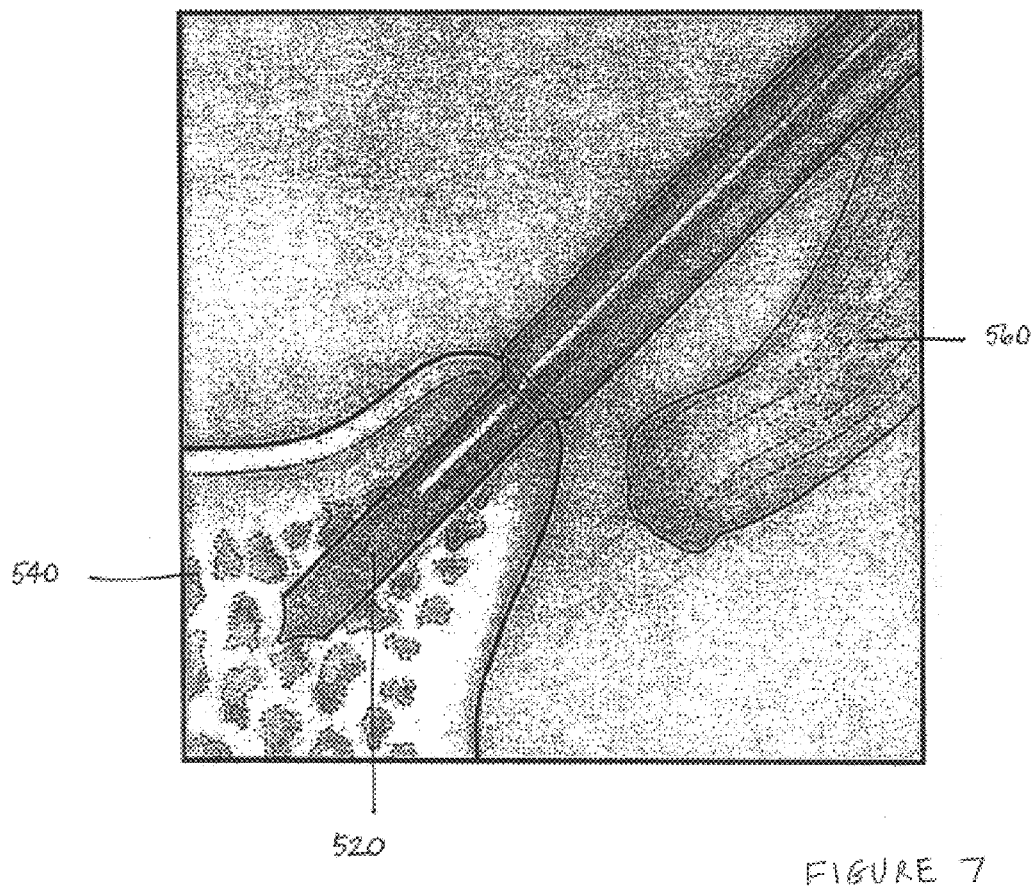
FIG. 7 is a view of a bore being drilled in bone for receiving a suture anchor system.

Referring to FIG. 7, a bore 520 is formed in a bone 540. The diameter of the bore 520 should be slightly larger than the outer diameter of the suture anchor 12. In an exemplary embodiment, the diameter of the bore 520 is approximately 3.5 to 4.7 mm when the outer diameter of the anchor 12, 110 is about 4 mm. It is contemplated that the outer diameter of the suture anchor 12, 110 will increase about 1.0 mm when fully expanded. The length of the bore must be of sufficient length to allow for complete seating of the suture anchor 12, 110, and to enable the depth of the anchor to be adjusted to help control the tightness of the first suture loop 80. The actual length of the bore 520 will depend upon the length of the first suture loop 80 and the thickness of the detached tissue 560.

Figure 8:
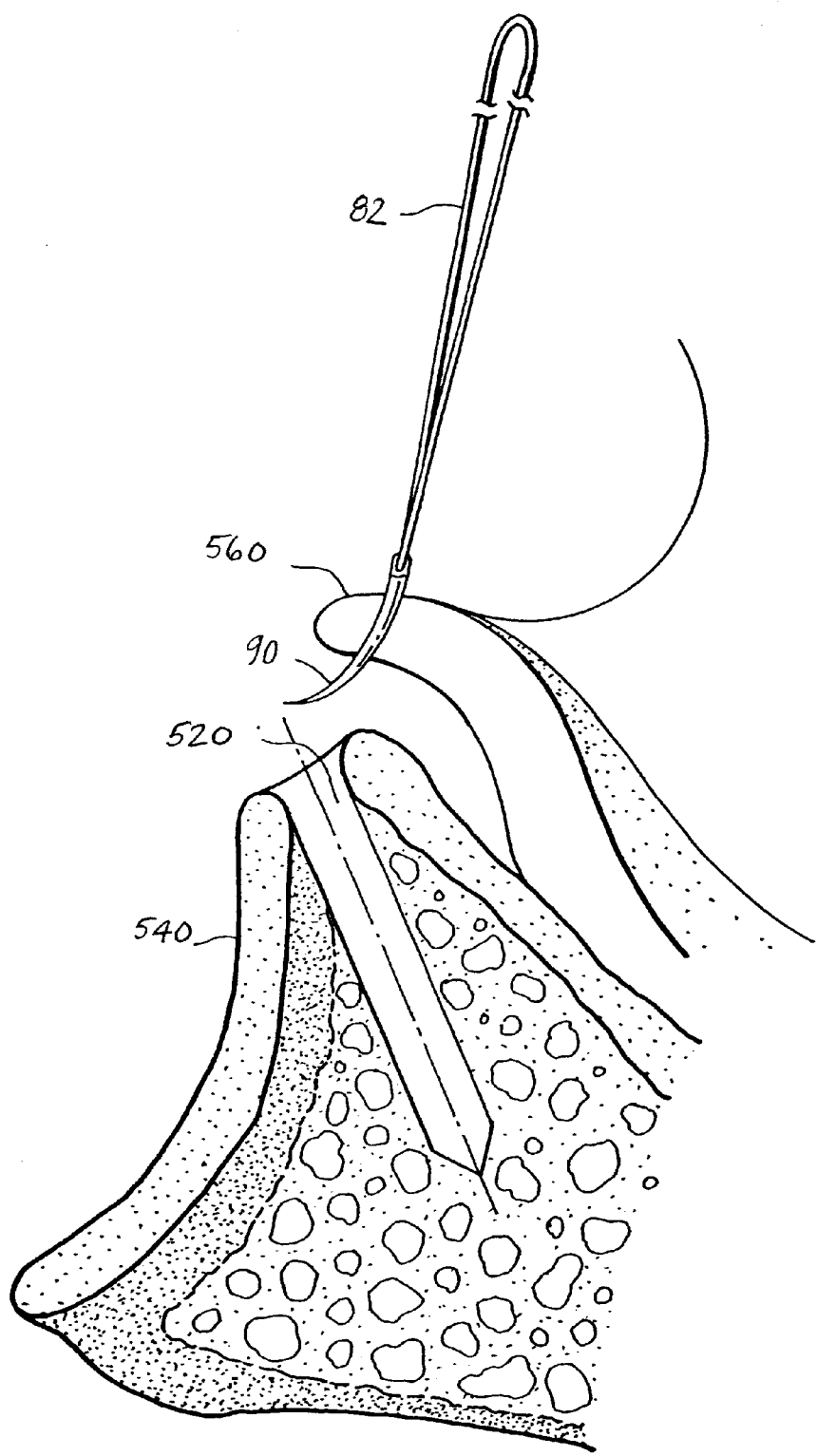
FIG. 8 is a view of a portion of the suture anchor system engaged with a detached tissue.
Figure 9:
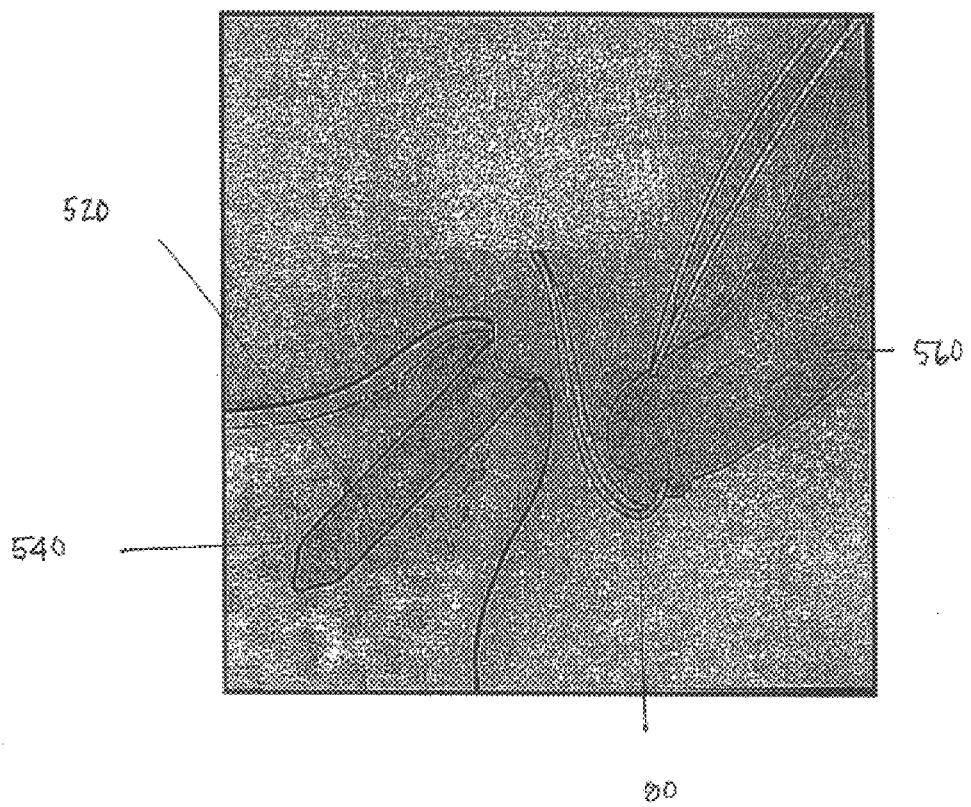
FIG. 9 is a view of the detached tissue with the second suture loop extending therethrough.

As shown in FIG. 8, the suture needle is then passed through the detached tissue 56. The suture needle 90 and the attached second suture loop 82 are pulled through the detached tissue 560 to advance the interlocked first loop 80 through the tissue, as illustrated in FIG. 9. If the procedure is being performed arthroscopically, the suture needle 90a and the tool with which it is associated will be pulled from, and exit through, an exit portal (not shown).

Alternatively, in embodiments that utilize the needle 90a, shown in FIG. 6, the needle 90a may penetrate the detached tissue 560. The actuator 48 is then selectively moved so as to disengage the suture loop closure 44 and the attached second suture loop 82 from the needle 90a. The suture needle 90a may then be withdrawn from the patient's body from the portal through which the needle entered. A suture grasper or retrograder (not shown) may be used to pull the remaining portion of the second loop 18 through the detached tissue 560.

Figure 10:
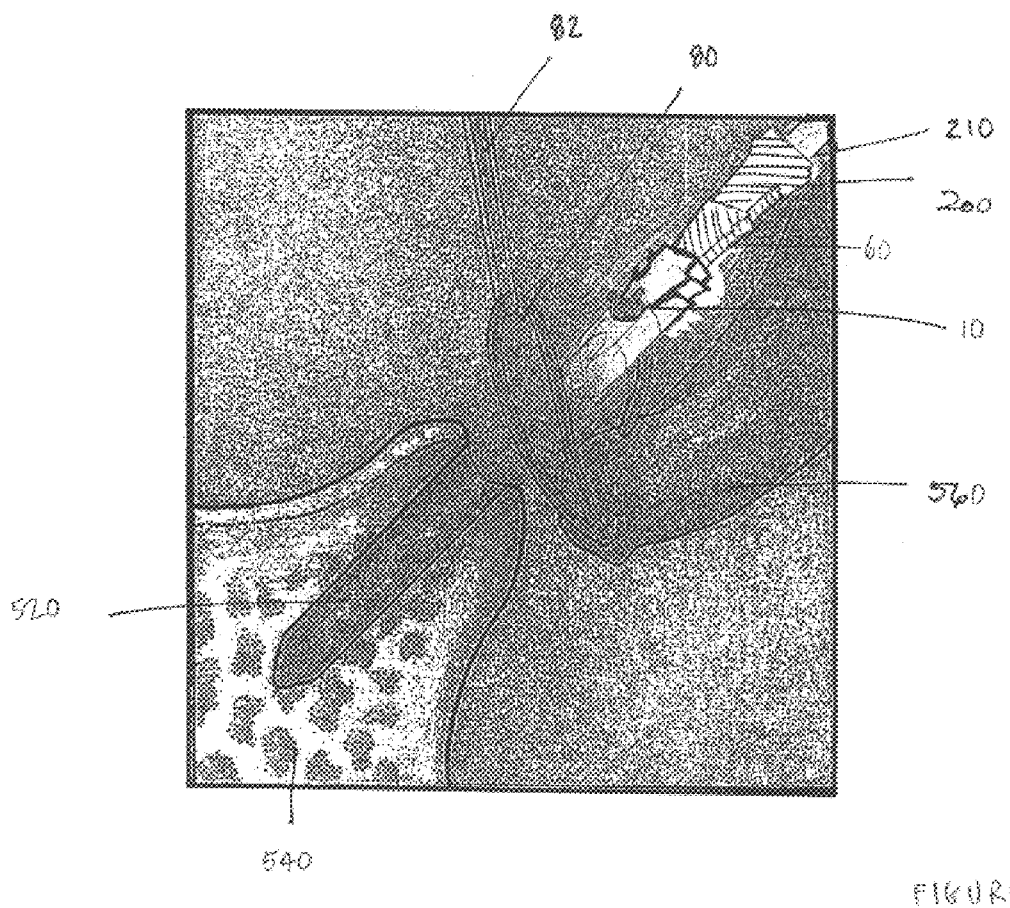
FIG. 10 is a view of a portion of the suture anchor system of FIG. 1 before the suture anchor is inserted into a bone.
Figure 11:
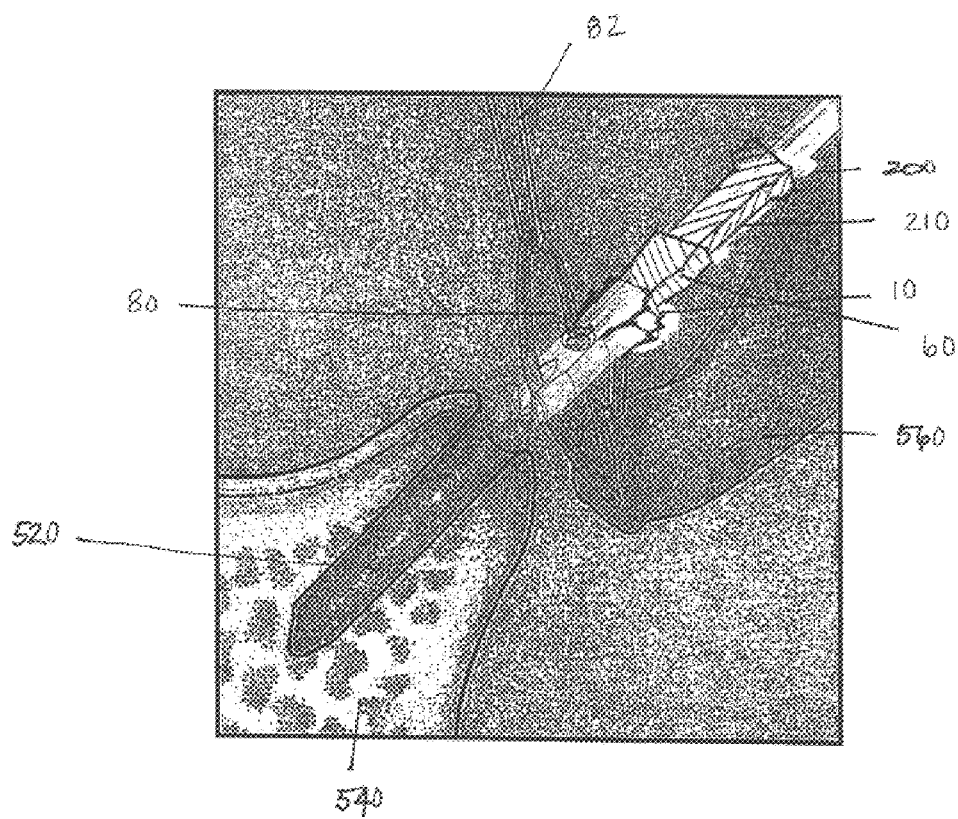
FIG. 11 is a view of a portion of the suture anchor system of FIG. 1 showing the first suture loop being engaged.
Figure 12:
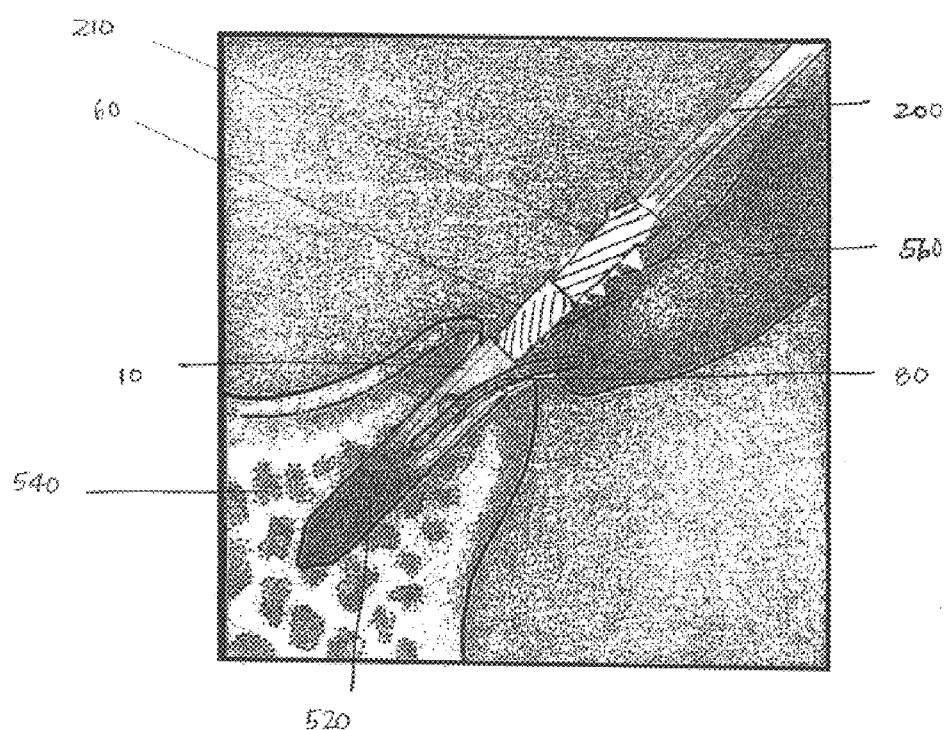
FIG. 12 is a view of a portion of the suture anchor system of FIG. 1 with the suture anchor inserted into a bone.

In FIG. 10, the first suture loop 80 is positioned over the bore 520 by manipulating the position of the second suture loop 82. When the first suture loop 80 is in its desired position, the insertion tool 200 is maneuvered so that a portion of the first suture loop 80 is seated in the suture-engaging groove 42 of the suture anchor 12, as shown in FIG. 11. Once the first suture loop 80 is so seated, the anchor 10 is aligned with the bore 520, and the suture anchor 12 is then inserted into the bore 520. When the suture anchor 12 is partially inserted, as illustrated in FIG. 12, the second suture loop 82 can be cut and discarded along with the suture needle 90.

Figure 13:
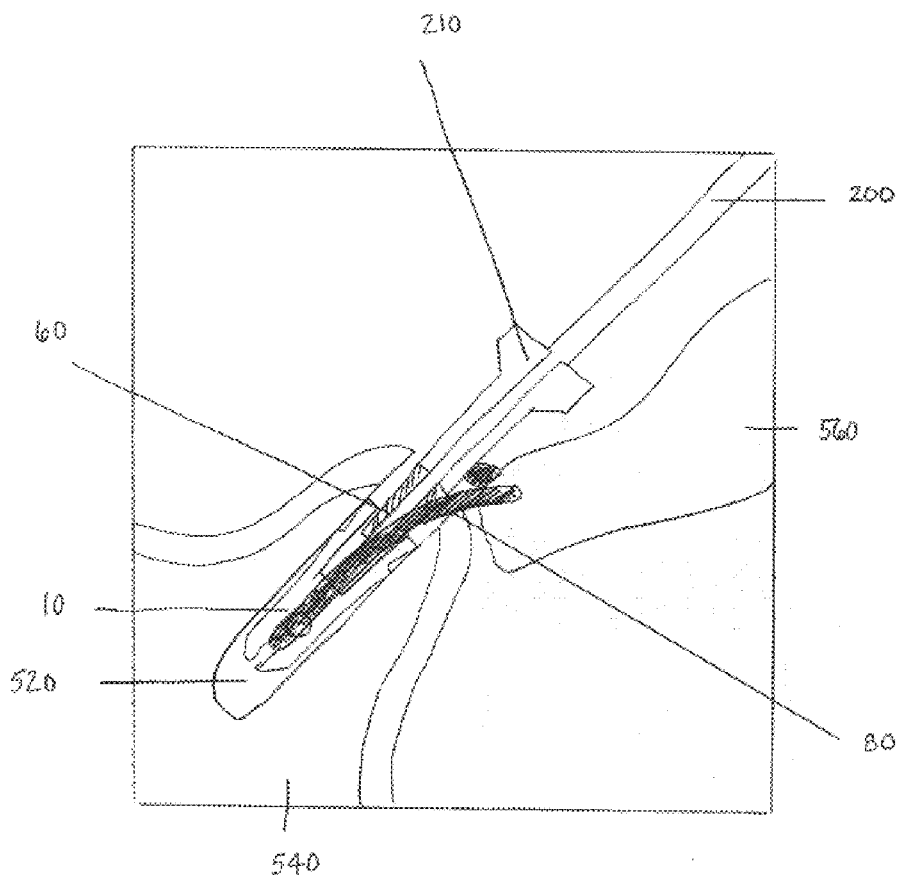
FIG. 13 is a cross-sectional view of a portion of the suture anchor system of FIG. 12.
Figure 14:
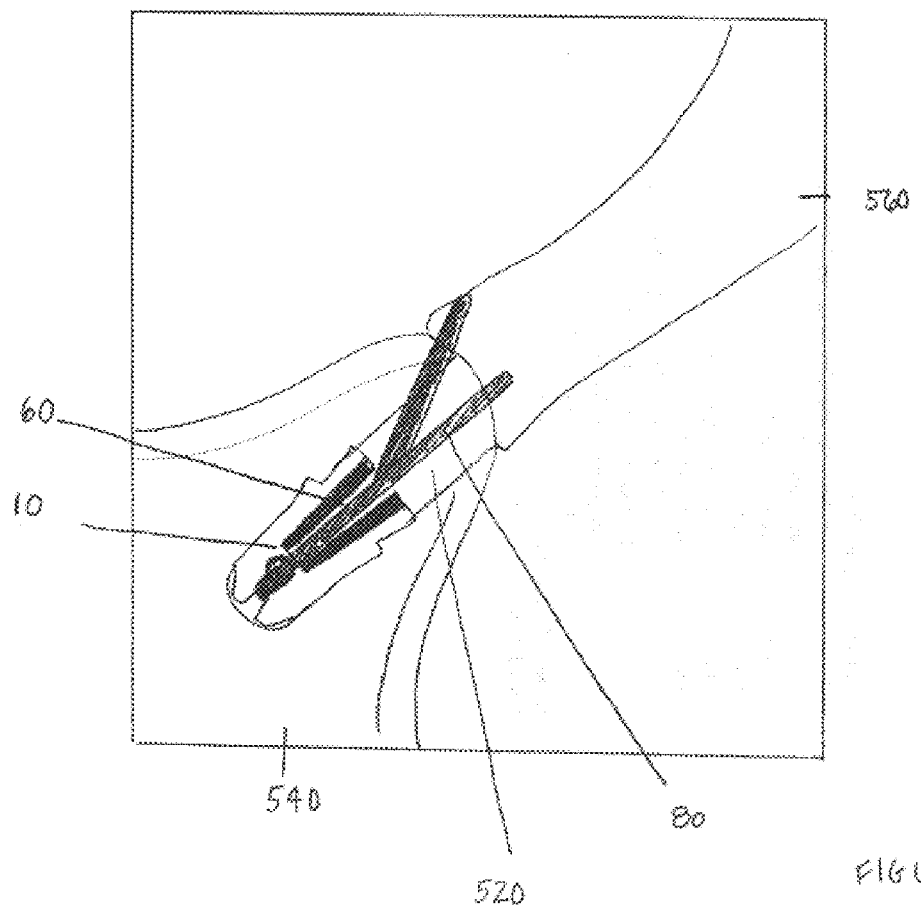
FIG. 14 is a cross-sectional view of a tissue attached to a bone, and a fully seated suture anchor, using the system and method of the invention.

Referring to FIG. 13, when the suture anchor 10 is advanced all the way into the bore 520, the pusher 210 is deployed to drive the expander pin 60 into the bore 22 of the expandable sleeve 20. As the expander pin 60 is inserted, the expandable sleeve 20 will radially expand, causing the sleeve 20 to wedge into the bone 540. When the expander pin 60 is completely inserted, as shown in FIG. 14, the expandable sleeve 20 is fully expanded and anchored in a frictional fit within the bore 520 of the bone. The result is a snug, anatomically correct attachment of the detached tissue 560 to the bone 540. Once the anchor 12 is inserted into bore 520, the anchor 12 is disengaged from the insertion tool 200 and the insertion tool 200 is removed.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A system for anchoring tissue to bone, comprising:
   a suture anchor having proximal and distal ends, wherein a suture-engaging tip is present at the distal end of the anchor and a separate, radially expandable sleeve, having a bore formed longitudinally therein, is attached to the suture-engaging tip and forms a proximal end of the suture anchor;
   a first loop of suture thread attached to the suture-engaging tip;
   a second loop of suture thread interlocked with the first loop of suture thread; and
   a suture needle having a first, tissue penetrating end and a second, trailing end, wherein the suture needle is attached to the second loop of suture thread.

2. The system of claim 1, further comprising an expander pin adapted to be inserted into the bore of the sleeve to effect radial expansion of the sleeve.

3. The system of claim 2, wherein the expandable sleeve has two substantially flat, longitudinally extending portions formed on opposite sides of the sleeve, between a proximal end and a distal end of the sleeve.

4. The system of claim 3, wherein a proximal end of the tip includes a first threaded region and a distal end of the sleeve includes a complementary threaded region, enabling the tip to be threadingly connected to the sleeve.

5. The system of claim 4, wherein the proximal end of the tip has an internally threaded bore formed therein.

6. The system of claim 5, wherein the first threaded region of the tip is formed on an outer surface of the tip.

7. The system of claim 6, further comprising an elongate insertion tool having a proximal, handle end, an externally threaded distal end that is matable with the internally threaded bore of the tip, and a shaft that is able to be disposed within the bore of the sleeve in a clearance fit.

8. The system of claim 7, wherein the expander pin has a longitudinal bore extending therethrough from a proximal end to a distal end thereof, the longitudinal bore having an inner diameter enabling it to be disposed on the shaft of the insertion tool in a first position proximally adjacent to and abutting the sleeve, and selectively moveable to a second position disposed between the shaft and an inner surface of the sleeve in an interference fit with the sleeve.

9. The system of claim 8, wherein the positioning of the expander pin in the second position causes the sleeve to radially expand from a first outer diameter to a second outer diameter.

10. The system of claim 9, wherein the difference between the first diameter and the second diameter is in the range of about 1.0 to 1.5 mm.

11. The system of claim 10, wherein the expander pin is formed from a bioabsorbable material.

12. The system of claim 11, wherein the pin is made from a material selected from the group consisting of polylactic acid and polysulfone.

13. The system of claim 11, wherein the expandable sleeve is formed from a polymeric material.

14. The system of claim 13, wherein the expandable sleeve is made from a material selected from the group consisting of high density polyethylene and polypropylene.

15. The system of claim 1, wherein the tip includes a suture thread-engaging groove for seating a portion of the first loop of suture thread.

16. The system of claim 1, wherein the expandable sleeve comprises at least one external surface feature effective to enhance bone engagement.

17. The system of claim 16, wherein the at least one surface feature comprises a plurality of ridges.

18. The system of claim 10, wherein the expander pin includes at least one surface feature effective to assist in the radial expansion of the sleeve.

19. The system of claim 18, wherein the at least one surface feature of the expander pin comprises a plurality of tapered ridges wherein a diameter of the expander pin at a distal part of the ridge is smaller than a diameter of the expander pin at a proximal part of the ridge.

20. A system for anchoring tissue to bone, comprising:
   an expandable base member having a distal end and a proximal end, the proximal end having a bore extending longitudinally therein and at least part of the proximal end being selectively radially expandable;
   a first loop of suture thread attached to the base member;
   a second loop of suture thread interlocked with the first loop of suture thread;
   a suture needle having a first, tissue penetrating end and a second, trailing end, wherein the suture needle is attached to the second loop of suture thread; and an expander pin, selectively disposable within the bore of the base member to radially expand the base member from a first outer diameter to a second outer diameter.

21. The system of claim 20, wherein the distal end of the base member includes a suture thread-engaging groove.

22. The system of claim 20, wherein the proximal end of the base member includes two opposed sides, each having a longitudinally extending slit formed therein.

23. The system of claim 22, wherein the two opposed sides are substantially flat.

24. The system of claim 22, wherein the proximal end of the base member has two opposed, radially expandable sides, the radially expandable sides being adjacent to the two opposed sides.

25. The system of claim 24, wherein the two opposed radially expandable sides each have at least one bone engaging positive surface feature formed therein.

26. The system of claim 25, wherein the bone engaging positive surface feature is a ridge having a distally facing ramped surface and a proximally facing surface with an end wall that is substantially perpendicular to a longitudinal axis of the member base.

27. The system of claim 26, wherein the expander pin includes wedge-like positive surface features effective to interact with the longitudinally extending slits of the base member to radially expand the proximal end of the base member.

28. The system of claim 20, wherein the bore of the base member has internal threads formed at a distal portion of the bore.

29. The system of claim 28, further comprising an elongate insertion tool having a proximal, handle end, a distal end with external threads formed therein, wherein the external threads are complementary to the internal threads of the base member, and a shaft that is able to be disposed within the bore of the base member in a clearance fit.

30. The system of claim 29, wherein the insertion tool further includes a pusher member slidably mounted around the shaft, the pusher member having a distal end proximally adjacent to and abutting a proximal end of the expander pin, such that the pusher member can be selectively advanced to be positioned between the shaft and an inner surface of the proximal end of the base member to effect the radial expansion of the base member.

31. The system of claim 30, wherein the difference between the first diameter and the second diameter is in the range of 1.0 to 1.5 mm.

32. The system of claim 27, wherein the longitudinally extending slits of the base member have a shape complementary to the wedge-like positive surface features of the expander pin and a size sufficient to receive the wedge-like positive surface features.

33. The system of claim 32, wherein positioning the expansion pin within the base member causes an irreversible interlocking of the wedge-like positive surface within the longitudinally extending slits.

34. The system of claim 20, wherein the base member is formed from a bioabsorbable material.

35. The system of claim 34, wherein the bioabsorbable material is selected from the group consisting of polylactic acid and polysulfone.

36. The system of claim 20, wherein the expansion pin is formed from a bioabsorbable material.

37. The system of claim 36, wherein the bioabsorbable material is selected from the group consisting of polylactic acid and polysulfone.

38. A suture anchor, comprising:
a first component including a tip having a suture thread-engaging groove formed therein, and a through-hole extending through the tip in a direction transverse to a longitudinal axis of the suture anchor;
a second component having an external surface with at least one positive surface feature formed thereon, at least a portion of the second component being selectively radially expandable; and
a bore extending into the second component of the suture anchor from the proximal end thereof, the bore being parallel with the longitudinal axis of the suture anchor.

39. The suture anchor of claim 38, wherein the first component is separate from the second component.

40. The suture anchor of claim 39, wherein the first component and the second component are threadingly engaged with each other.

41. The suture anchor of claim 39, wherein the bore extends entirely through the second component of the suture anchor from a proximal end to a distal end thereof.

42. The suture anchor of claim 41, wherein the at least one positive surface feature comprises a plurality of wedge-like fins.

43. The suture anchor of claim 42, wherein each wedge-like fin has a ramped surface distal of a distal facing endwall that is substantially transverse to the longitudinal axis of the suture anchor.

44. The suture anchor of claim 43, wherein the suture anchor further comprises a separate expansion element having an outside diameter sufficient to fit within the bore of the second component in an interference fit to cause the second component to radially expand.

45. The suture anchor of claim 44, wherein the external surface of the expansion element has at least one positive surface feature effective to assist in the radial expansion of the second component from a first diameter to a second diameter.

46. The suture anchor of claim 45, wherein the positive surface feature is a wedge-like structure having a proximal portion that is raised relative to a distal end thereof.

47. The suture anchor of claim 46, wherein a distal portion of the bore includes internal threads.

48. The suture anchor of claim 39, wherein the tip is made from a material selected from the group consisting of polylactic acid and polysulfone.

49. The suture anchor of claim 39, wherein the second component is made from a material selected from the group consisting of high density polyethylene and polypropylene.

50. The suture anchor of claim 44, wherein the expansion element is bioabsorbable and is made from a material selected from the group consisting of polylactic acid and polysulfone.

51. The suture anchor of claim 45, wherein the difference between the first diameter and the second diameter is in the range of about 1.0 to 1.5 mm.

52. The suture anchor of claim 38, wherein the first and second components of the suture anchor are made from the same material and are integral with each other.

53. The suture anchor of claim 52, wherein a proximal end of the second component has longitudinally extending slits formed therein on opposite sides of the second component.

54. The suture anchor of claim 52, wherein the bore terminates proximal of the through-hole and does not communicate with the through-hole.

55. The suture anchor of claim 54, wherein the at least one positive surface feature comprises a plurality of wedge-like fins.

56. The suture anchor of claim 55, wherein each wedge-like fin has a ramped surface distal of a distal facing endwall that is substantially transverse to the longitudinal axis of the suture anchor.

57. The suture anchor of claim 56, wherein the suture anchor further comprises a separate expansion element having an outside diameter sufficient to enable the expansion element to fit within the bore of the second component in an interference fit to effect radial expansion of the second component from a first diameter to a second diameter.

58. The suture anchor of claim 57, wherein the external surface of the expansion element has at least one positive surface feature effective to assist in the radial expansion of the second component from the first diameter to the second diameter.

59. The suture anchor of claim 58, wherein the expansion element has at least two positive surface features on opposite sides of the expansion element and each positive surface feature includes at least one wedge-like structure having a proximal portion that is raised relative to a distal end thereof.

60. The suture anchor of claim 59, wherein each of the at least one wedge-like structures is complementary in shape to the slits of the suture anchor.

61. The suture anchor of claim 59, wherein each of the at least one wedge-like structures has dimensions that enable it to fit within and irreversibly interlock with the slits of the suture anchor.

62. The suture anchor of claim 57, wherein the difference between the first diameter and the second diameter is in the range of about 1.0 to 1.5 mm.

63. The suture anchor of claim 52, wherein the suture anchor is made from a material selected from the group consisting of high density polyethylene and polypropylene.

64. The suture anchor of claim 57, wherein the expansion element is bioabsorbable.

65. The suture anchor of claim 64, wherein the expansion element is made from a material selected from the group consisting of polylactic acid and polysulfone.

* * * * *